United States Patent
Yoo et al.

(10) Patent No.: US 10,983,127 B2
(45) Date of Patent: Apr. 20, 2021

(54) DEVICE FOR DIAGNOSING COLORECTAL CANCER AND METHOD FOR PROVIDING COLORECTAL CANCER DIAGNOSIS INFORMATION

(71) Applicant: NATIONAL CANCER CENTER, Gyeonggi-do (KR)

(72) Inventors: Byong Chul Yoo, Gyeonggi-do (KR); Kyung Hee Kim, Seoul (KR); Jun Hwa Lee, Gyeonggi-Do (KR)

(73) Assignee: NATIONAL CANCER CENTER, Gyeonggi-Do (KR)

( * ) Notice: Subject to any disclaimer, the term of this patent is extended or adjusted under 35 U.S.C. 154(b) by 267 days.

(21) Appl. No.: 16/332,405

(22) PCT Filed: Sep. 1, 2017

(86) PCT No.: PCT/KR2017/009599
§ 371 (c)(1),
(2) Date: Mar. 12, 2019

(87) PCT Pub. No.: WO2018/062704
PCT Pub. Date: Apr. 5, 2018

(65) Prior Publication Data
US 2020/0173996 A1    Jun. 4, 2020

(30) Foreign Application Priority Data
Sep. 28, 2016 (KR) .................. 10-2016-0125064

(51) Int. Cl.
*G01N 30/88* (2006.01)
*G01N 33/574* (2006.01)
*G01N 30/72* (2006.01)

(52) U.S. Cl.
CPC ... *G01N 33/57419* (2013.01); *G01N 30/7233* (2013.01); *G01N 30/88* (2013.01);
(Continued)

(58) Field of Classification Search
CPC ......... G01N 33/57419; G01N 30/7233; G01N 30/88; G01N 33/57488; G01N 2030/8813; G01N 33/57484
See application file for complete search history.

(56) References Cited

U.S. PATENT DOCUMENTS

2012/0326025 A1    12/2012  Weinberger et al.
2016/0299144 A1*   10/2016  Blume .............. G01N 33/57419

FOREIGN PATENT DOCUMENTS

WO    2009052186 A1    4/2009
WO    2013070839 A1    5/2013
WO    2015091962 A1    6/2015

OTHER PUBLICATIONS

International Search Report, PCT/KR2017/009599 dated Dec. 4, 2017.
(Continued)

*Primary Examiner* — Jennifer Wecker
*Assistant Examiner* — Michael Paul Shimek
(74) *Attorney, Agent, or Firm* — Porzio Bromberg & Newman P.C.

(57) ABSTRACT

The present invention relates to a device of diagnosing a colorectal cancer and a method for providing colorectal cancer diagnosis information. A colorectal cancer diagnosing device according to the present invention includes: an input unit which acquires mass spectrometry data measured from a biological sample; a concentration detecting unit which measures a concentration of nudifloramide from the acquired mass spectrometry data; and a diagnosing unit which determines diagnosis information of the colorectal cancer based on a measurement result of the concentration detecting unit.

8 Claims, 3 Drawing Sheets

(52) U.S. Cl.
CPC ............ *G01N 33/57488* (2013.01); *G01N 2030/8813* (2013.01)

(56) References Cited

OTHER PUBLICATIONS

Brown et al., Metabolomics and metabolic pathway networks from human colorectal cancers, adjacent mucosa, and stool, Cancer & Metabolism, 2016, 4:11.

Fukui et al., A Plasma Metabolomic Investigation of Colorectal Cancer Patients by Liquid Chromatography-Mass Spectrometry, The Open Analytical Chemistry Journal, 2010, 4, 1-9.

European Search Report dated Feb. 28, 2020 in corresponding European Patent Application No. 17856590.9.

Chinese Office Action dated Aug. 12, 2020 in corresponding Chinese Patent Application No. 201780059469.4.

Metabolomics and metabolic pathway networks from human colorectal cancers, adjacent mucosa, and stool (including "Supplemental Tables"), Dustin G. Brown et al., Cancer & Metabolism, 2016, 4(11).

A Plasma Metabolomic Investigation of Colorectal Cancer Patients by Liquid Chromatography—Mass Spectrometry, Yousuke Fukui et al., The Open Analytical Chemistry Journal, 2010, 4, pp. 1-9.

Metabolomic Biomarkers for Colorectal Cancer, Farshad Farshidfar, University of Calgary, 2016 doctoral thesis, https://prism.ucalgary.ca/handle/11023/3101.

\* cited by examiner

DEVICE FOR DIAGNOSING COLORECTAL CANCER AND METHOD FOR PROVIDING COLORECTAL CANCER DIAGNOSIS INFORMATION

TECHNICAL FIELD

The present invention relates to a device for diagnosing a colorectal cancer and a method for providing colorectal cancer diagnosis information.

BACKGROUND ART

Cancer is a disease in which cells infinitely proliferate to disturb functions of normal cells. Representative cancers include a lung cancer, a gastric cancer (GC), a breast cancer (BRC), a colorectal cancer (CRC), and an ovarian cancer (OVC), but actually, the cancers may be generated in any of tissues.

In the early period, the cancer is diagnosed based on an external change of biological tissues in accordance with the growth of cancer cells. However, in recent years, the cancer diagnosis and detection using a very small amount of biomolecules existing in tissues or cells of living bodies, such as blood, glyco chain, or DNA have been attempted. However, cancer diagnosis methods which diagnose the cancer using a tissue sample obtained by the biopsy or using imaging are most commonly used.

Among them, the biopsy causes a great deal of pain of the patient and is very costly. Further, it takes a long time to diagnose the cancer. Further, when a patient actually gets a cancer, there is a risk of cancer metastasis during the biopsy. Further, when a tissue sample cannot be obtained by the biopsy, it is impossible to diagnose the disease until a suspicious tissue is removed through a surgical operation.

In the meantime, a method for diagnosing the cancer through a biostatistical analysis on a low mass ion extracted from a biological sample has been proposed in recent years, but it takes a long time to analyze the result.

DISCLOSURE

Technical Problem

An object of the present invention is to provide a device of diagnosing a colorectal cancer and a method for providing colorectal cancer diagnosis information with a high precision at a short analysis time.

Technical Solution

According to an aspect of the present invention, a colorectal cancer diagnosing device includes: an input unit which acquires mass spectrometry data measured from a biological sample, a concentration detecting unit which measures a concentration of nudifloramide from the acquired mass spectrometry data; and a diagnosing unit which determines diagnosis information of the colorectal cancer based on a measurement result of the concentration detecting unit.

The concentration detecting unit may further measure at least one of dodecanoylcarnitine and trans-2-dodecenoylcarnitine.

The concentration detecting unit may further measure a concentration of dodecanoylcarnitine and the diagnosing unit may determine diagnosis information of the colorectal cancer based on a concentration ratio of nudifloramide and dodecanoylcarnitine.

The concentration detecting unit may further measure a concentration of trans-2-dodecenoylcarnitine and the diagnosing unit may determine diagnosis information of the colorectal cancer based on a concentration ratio of nudifloramide and trans-2-dodecenoylcarnitine.

The mass spectrometry data may be acquired from a liquid chromatography mass spectrometer (LC-MS) and the mass spectrometer may be any one of a triple TOF and triple Quadrupole.

According to an aspect of the present invention, a colorectal cancer diagnosing device may include a determining unit which determines diagnosis information of a colorectal cancer based on a concentration of nudifloramide measured from a biological sample and at least one of concentrations of dodecanoylcarnitine and trans-2-dodecenoylcarnitine.

The determining unit may determine the colorectal cancer diagnosis information based on a ratio of a concentration of nudifloramide and a concentration of at least one of dodecanoylcarnitine and trans-2-dodecenoylcarnitine.

The concentration may be acquired from a liquid chromatography mass spectrometer and the mass spectrometer may be any one of a triple TOF and triple Quadrupole.

Another aspect of the present invention, a method for providing information for colorectal cancer diagnosis includes: acquiring a concentration of nudifloramide and a concentration of at least one of dodecanoylcarnitine and trans-2-dodecenoylcarnitine from a biological sample and providing diagnosis information of a colorectal cancer based on a concentration ratio of the concentration of nudifloramide and the concentration of at least one of dodecanoylcarnitine and trans-2-dodecenoylcarnitine.

The concentration may be acquired from mass spectrometry of a biological sample.

The mass spectrometry may be acquired from a liquid chromatography mass spectrometer and the mass spectrometer may be any one of a triple TOF and triple Quadrupole.

Advantageous Effects

According to the present invention, provided are a device of diagnosing a colorectal cancer and a method for providing colorectal cancer diagnosis information with a high precision at a short analysis time.

MODES OF THE INVENTION

In the present invention, "biological samples" include samples such as whole blood, serum, plasma, urine, stool, sputum, saliva, tissues, cells, cell extracts, and in vitro cell cultures, but are not limited thereto. In the following exemplary embodiments, serums of patients or non-patients are used as biological samples.

The present invention is based on the findings that Nudifloramide (hereinafter, abbreviated as "2PY") is useful as a marker of colorectal cancer.

A formal title of nudifloramide is N-Methyl-2-pyridoxone-5-carboxamide; 1,6-Dihydro-1-methyl-6-oxonicotinamide; 3-Carbamoyl-1-methyl-6-pyridone and a structural formula is as follows.

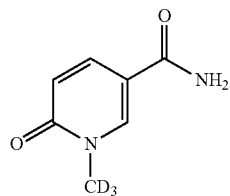 [SMILES: [2H]C([2H])([2H])n1cc(C(N)=O)ccc1=O]

Nudifloramide is present in a high concentration in patients with colorectal cancer.

The present invention is also based on the findings that dodecanoylcarnitine (hereinafter, abbreviated as "DC") and trans-2-dodecenoylcarnitine (hereinafter, abbreviated as "T2DC") are useful as a marker of colorectal cancer.

DC and T2DC are present in low concentrations in patients with colorectal cancer.

In the present invention, the colorectal cancer is diagnosed based on concentrations of the markers but is not limited thereto. The concentration may be measured using a mass peak area measured by a mass spectrometer.

More specifically, the concentration may be measured using a liquid chromatography-mass spectrometry (LC-MS) and the mass spectrometry may be performed using Triple-TOF or Triple Quadrupole.

In the exemplary embodiment of the present invention, the colorectal cancer may be diagnosed using a concentration ratio between three markers. The concentration ratio is not limited thereto and at least one of a concentration ratio of 2PY/DC and a concentration ratio of 2PY/T2DC may be used.

As a reference value (cutoff) to determine whether it is a colorectal cancer, for example, 2PY/DC may be 20 to 40, 25 to 32, or 27 to 30 and 2PY/T2DC may be 30 to 50, 35 to 45, or 38 to 42. When a measurement value exceeds the reference value, it is determined as a colorectal cancer. The reference value may be set differently for every subject in consideration of a gender, an age, a disease history, a stage of cancer, and a health status of the subject.

According to the present invention as described above, only concentrations for markers are measured and the colorectal cancer may be diagnosed from the concentration ratio between markers. Therefore, the colorectal cancer may be quickly diagnosed.

Hereinafter, the present invention will be described in more detail with reference to the drawings.

The accompanying drawings are merely examples illustrated to more specifically describe the technical spirit of the present invention so that the spirit of the present invention is not limited to the accompanying drawings.

Figure 1:
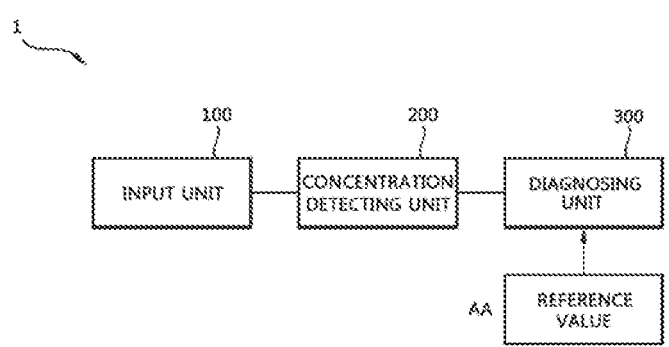
FIG. 1 is a block diagram of a colorectal cancer diagnosis device according to an exemplary embodiment of the present invention.

FIG. 1 is a block diagram of a colorectal cancer diagnosis device according to an exemplary embodiment of the present invention.

The colorectal cancer diagnosis device 1 includes an input unit 100, a concentration detecting unit 200, and a diagnosing unit 300.

The input unit 100 acquires mass spectrometry data detected from a biological sample. The mass spectrometry data includes only data for a marker and the marker includes 2 PY. The marker may further include at least one of DC and T2 DC.

The mass spectrometry data may be a mass spectrometry spectrum or a mass peak area for a marker.

The concentration detecting unit 200 measures (calculates) a concentration of the marker from the mass spectrometry data.

When input data is a mass spectrometry spectrum, the concentration may be measured by measuring a mass peak area of a peak corresponding to the marker or when the input data is a mass peak area for the marker, the mass peak area may be used as it is.

According to another exemplary embodiment, an appropriate factor is added to the deduced mass peak area or an additional mathematical treatment is applied thereto to be used as a concentration. The reference value may vary by the factor or the mathematical treatment.

The diagnosing unit 300 determines a positive colorectal cancer or a negative colorectal cancer using the measured concentration of the marker. During this process, the diagnosing unit 300 may use only the concentration of 2 PY or use any one of a concentration ratio of 2 PY/DC and a concentration ratio of 2 PY/T2 DC.

A reference value for the concentration ratios of 2 PY/DC and 2 PY/T2 DC is set in the diagnosing unit 300 and different reference values may be set depending on subjects (samples).

In addition, the diagnosing device 1 may further include a display unit which notifies a diagnosis result and the output unit may be a display device or a printer.

The diagnosing device 1 described above may be modified in various forms. For example, when the concentration of the marker is directly input from the outside, the concentration detecting unit 200 may be omitted.

In the meantime, the present invention provides a colorectal cancer diagnosing method.

The colorectal cancer diagnosing method includes acquiring mass spectrometry data measured from a biological sample, measuring a concentration of nudifloramide from the acquired mass spectrometry data, and diagnosing a colorectal cancer based on a concentration measuring result.

During the measuring of a concentration, at least one of dodecanoylcarnitine and trans-2-dodecenoylcarnitine may be further measured.

In the measuring of a concentration, a concentration of dodecanoylcarnitine is further measured and the colorectal cancer may be diagnosed based on a concentration ratio of nudifloramide and dodecanoylcarnitine.

In the measuring of a concentration, a concentration of trans-2-dodecenoylcarnitine is further measured and the colorectal cancer may be diagnosed based on a concentration ratio of nudifloramide and trans-2-dodecenoylcarnitine.

The mass spectrometry data may be acquired from a liquid chromatography mass spectrometer (LC-MS) and the mass spectrometer may be any one of a triple TOF and triple Quadrupole.

The colorectal cancer diagnosing method may further include determining diagnosis information of a colorectal cancer based on a concentration of nudifloramide and a concentration of at least one of dodecanoylcarnitine and trans-2-dodecenoylcarnitine measured from a biological sample.

The determination may be performed based on a ratio of a concentration of nudifloramide and a concentration of at least one of dodecanoylcarnitine and trans-2-dodecenoylcarnitine.

Hereinafter, the present invention will be described in detail with reference to the following experimental examples.

Collection of Serum

Serum was collected from 190 normal control subjects, 81 colorectal cancer patients, 20 gastric cancer patients, 100 lung cancer patients, and 13 ovarian cancer patients.

Preparation for Measuring Concentration 1 ml of water, 2 ml of methanol, and 0.9 ml of dichloromethane were added to 50 μl of serum and shaken to be well mixed and then left on ice for 30 minutes. Next, 1 ml of water and 0.9 ml of dichloromethane were added and mixed well and then centrifuged at 1500 rpm for 10 minutes at a room temperature. After centrifugation, a supernatant was separated and dried using nitrogen gas.

Measurement of Concentration of Metabolome (Marker)

Dried metabolome extracts were dissolved in 0.1% formic acid and then analyzed using a liquid chromatography-mass spectrometry (LC-MS).

The used LC was Eksigent ultra LC 110-XL system and MS was AB Sciex Triple TOF 5600+ system. DuoSpray ion source is mounted in the MS. The analysis sample was input into the analyzing unit through Atlantis T3 sentry guard cartridge (3 mm, 2.1 10 mm; Waters) connected to Eksigent ultraLC 110-XL system and separated in Atlantis T3 column (3 mm, 2.1 100 mm; Waters).

As a solvent, two-step linear gradient (solvent A, 0.1% FA in water; solvent B, 100% Acetonitrile; with 1% solvent B for 2 min, 1 to 30% B for 6 min, 30 to 90% B for 8 min, 90% B for 4 min, 90 to 1% B for 1 min and 9 min in 1% B) was used.

One full scan (50 to 1,200 m/z range) and tandem mass spectrometry (MS/MS) of 10 most frequent parent ions (mass tolerance, 50 mDa collision energy, 35%) were performed on the MS.

Among MS spectra at the same time zone as a time zone when the metabolome corresponding to 2 PY, DC, and T2 DC passes through the LC, a mass peak area having the same mass value was calculated.

Analysis Result

Figure 2:
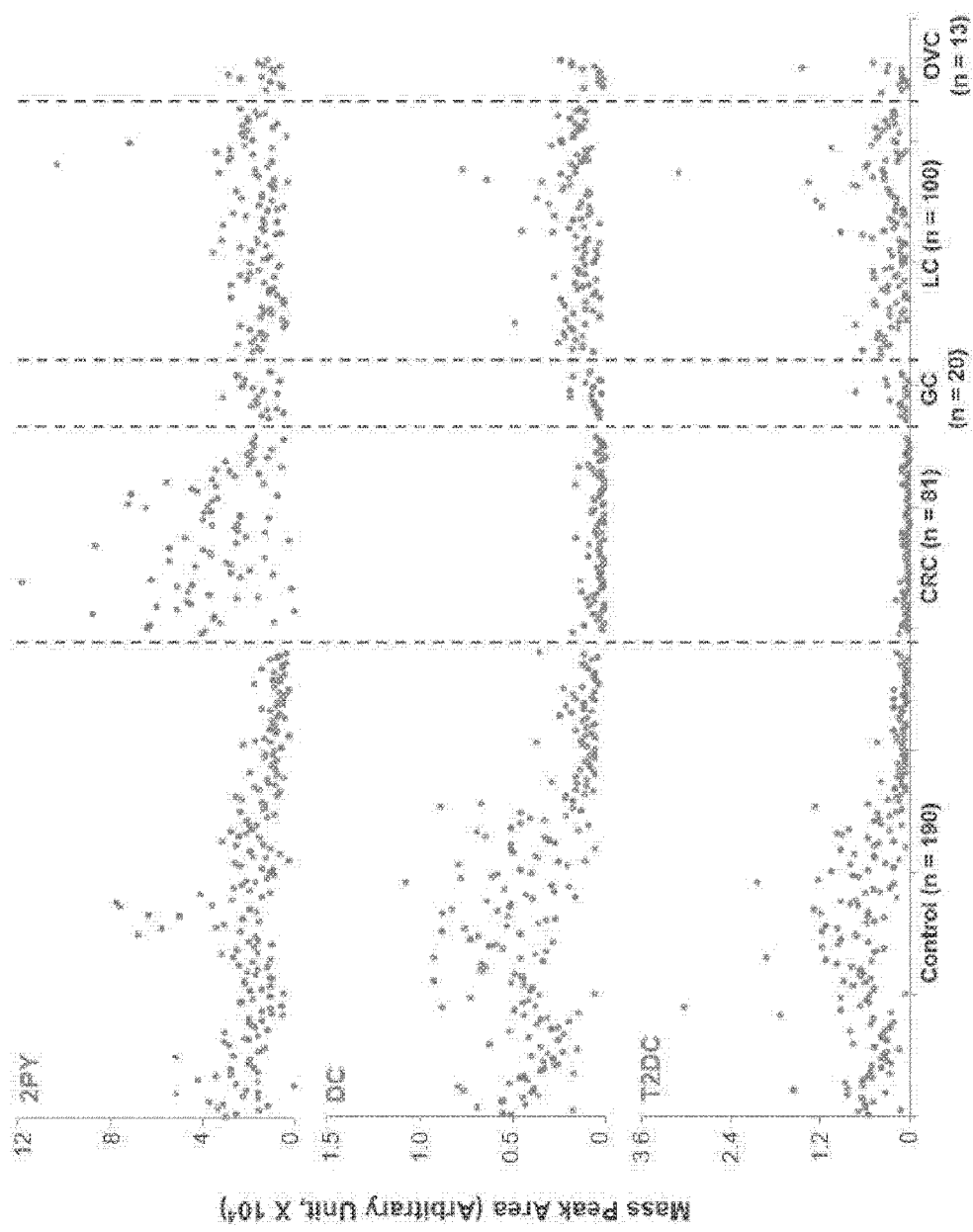
FIG. 2 illustrates a mass peak area which is proportional to concentrations of 2PY, DC, and T2DC in each sample.

FIG. 2 illustrates a mass peak area which is proportional to concentrations of 2PY, DC, and T2 DC in each sample.

It was understood that 2PY was measured to have a high concentration (a larger mass peak area) in the blood of the colorectal cancer patient, different from the normal control group or other cancer patients. Further, it was understood that concentrations of DC and T2DC were high (a larger mass peak area) in the blood of the normal control group different from the colorectal cancer patient and other cancer patient.

Figure 3:
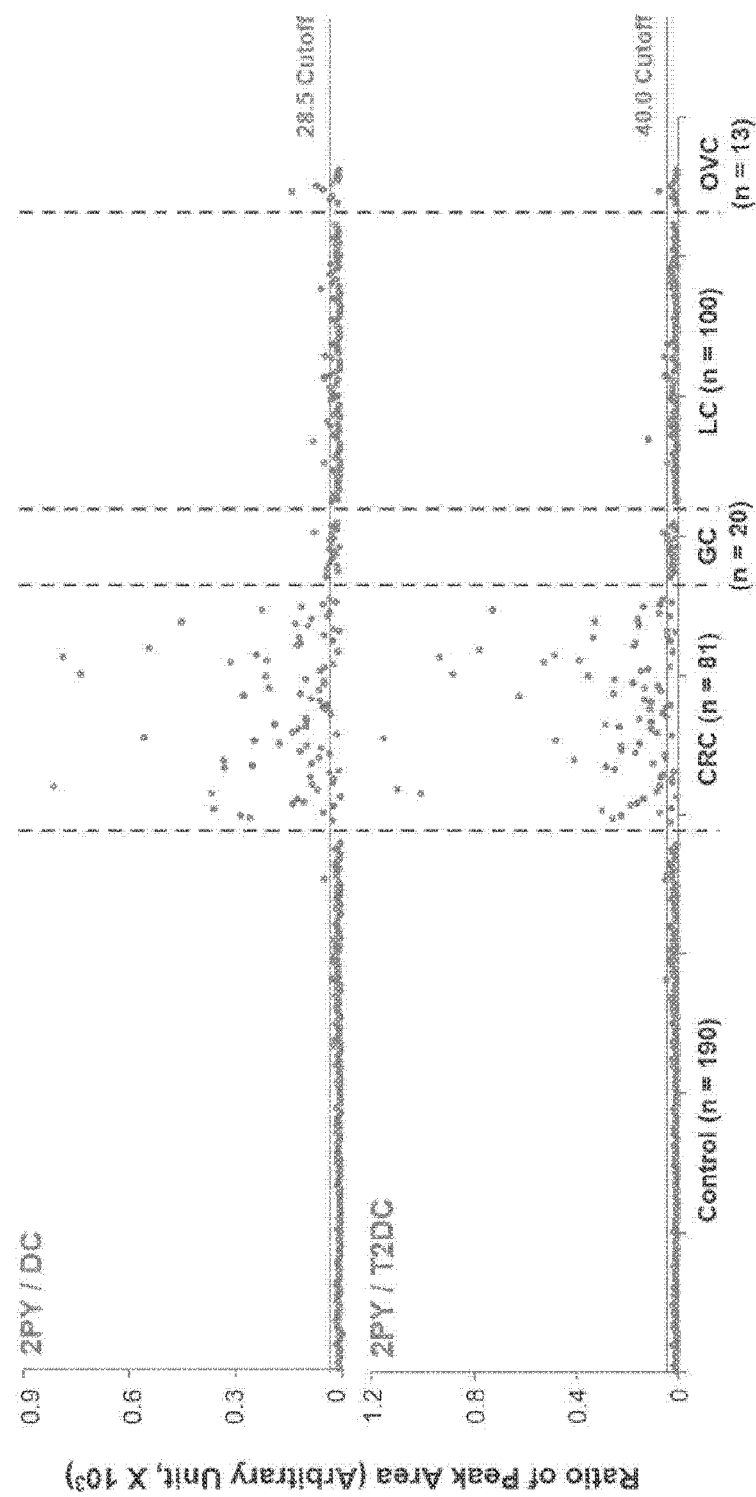
FIG. 3 illustrates a ratio of mass peak areas of 2PY/DC and 2PY/T2DC in each sample.

FIG. 3 illustrates a ratio of mass peak areas of 2 PY/DC and 2PY/T2 DC in each sample. In both cases, it was understood that the concentration ratios of 2PY/DC and 2PY/T2 DC were very high in the colorectal cancer patient.

In Tables 1 to 3, when the reference value (cutoff) of 2PY/DC is 28.5 and a reference value (cutoff) of 2PY/T2DC is 40, sensitivity and specificity for various cancers are represented.

As seen from Tables, the concentration ratios of the 2PY/DC and 2PY/T2DC have excellent sensitivity and specificity for the colorectal cancer.

TABLE 1

| 2PY/DC | | True | | | | |
|---|---|---|---|---|---|---|
| | | control | CRC | GC | LC | OVC |
| Predicted | Non-CRC | 189 | 13 | 15 | 86 | 9 |
| | CRC | 1 | 68 | 5 | 14 | 4 |

TABLE 2

| 2PY/T2DC | | True | | | | |
|---|---|---|---|---|---|---|
| | | control | CRC | GC | LC | OVC |
| Predicted | Non-CRC | 189 | 16 | 19 | 97 | 12 |
| | CRC | 1 | 65 | 1 | 3 | 1 |

TABLE 3

| | 2PY/DC | 2PY/T2DC |
|---|---|---|
| Sensitivity | 83.95% | 80.25% |
| Specificity | 92.57% | 98.14% |
| Positive Prediction Value | 73.91% | 91.55% |
| Negative Prediction Value | 95.83% | 95.20% |

The above-described exemplary embodiments are examples for describing the present invention, but the present invention is not limited thereto. The present invention may be carried out in various forms by those skilled in the art so that a technical scope of the present invention should be defined by the accompanying claims.

The invention claimed is:

1. A colorectal cancer diagnosing device, comprising:
   an input unit which acquires mass spectrometry data measured from a biological sample;
   a concentration detecting unit which is configured to measure a concentration of nudifloramide and a concentration of at least one of dodecanoylcarnitine and trans-2-dodecenoylcarnitine from a biological sample from the acquired mass spectrometry data; and
   a diagnosing unit which is configured to determine diagnosis information of the colorectal cancer based on a concentration ratio of nudifloramide and trans-2-dodecenoylcarnitine from the concentration detecting unit.

2. The colorectal cancer diagnosing device of claim 1, wherein the concentration detecting unit further measures a concentration of dodecanoylcarnitine and the diagnosing unit determines diagnosis information of the colorectal cancer based on a concentration ratio of nudifloramide and dodecanoylcarnitine.

3. The colorectal cancer diagnosing device of claim 1, wherein the mass spectrometry data is acquired from a liquid chromatography mass spectrometer (LC-MS) and the mass spectrometer is any one of a triple TOF and triple Quadrupole.

4. A colorectal cancer diagnosing device, comprising: a determining unit configured to determine diagnosis information of a colorectal cancer based on a concentration of nudifloramide and at least one of concentrations of dodecanoylcarnitine and trans-2- dodecenoylcarnitine measured from a biological sample by determining diagnosis information of the colorectal cancer based on a concentration ratio of a concentration of nudifloramide and a concentration of at least one of dodecanoylcarnitine and trans-2-dodecenoylcarnitine.

5. The colorectal cancer diagnosing device of claim 4, wherein the concentration is acquired from a liquid chromatography mass spectrometer and the mass spectrometer is any one of a Triple TOF and Triple Quadrupole.

6. A method for providing information for colorectal cancer diagnosis, the method comprising: acquiring a concentration of nudifloramide and a concentration of at least one of dodecanoylcarnitine and trans-2-dodecenoylcarnitine from a biological sample and providing diagnosis information of a colorectal cancer based on a concentration ratio of the concentration of nudifloramide and the concentration of at least one of dodecanoylcarnitine and trans-2-dodecenoylcarnitine.

7. The method for providing information for colorectal cancer diagnosis of claim 6, wherein the concentration is acquired from mass spectrometry of a biological sample.

8. The method for providing information for colorectal cancer diagnosis of claim 7, wherein the mass spectrometry is performed by a liquid chromatography mass spectrometer and the mass spectrometer is any one of a Triple TOF and Triple Quadrupole.

* * * * *